US008923952B2

(12) United States Patent
O'Connor et al.

(10) Patent No.: US 8,923,952 B2
(45) Date of Patent: Dec. 30, 2014

(54) SYSTEM AND METHOD FOR QUANTITATIVE MOLECULAR BREAST IMAGING

(75) Inventors: Michael K. O'Connor, Rochester, MN (US); Carrie B. Hruska, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1197 days.

(21) Appl. No.: 12/515,369

(22) PCT Filed: Dec. 10, 2007

(86) PCT No.: PCT/US2007/086991
§ 371 (c)(1),
(2), (4) Date: May 18, 2009

(87) PCT Pub. No.: WO2008/073897
PCT Pub. Date: Jun. 19, 2008

(65) Prior Publication Data
US 2010/0034734 A1     Feb. 11, 2010

Related U.S. Application Data

(60) Provisional application No. 60/869,419, filed on Dec. 11, 2006.

(51) Int. Cl.
*A61B 6/00* (2006.01)
*A61B 5/05* (2006.01)
*G01N 23/00* (2006.01)
*G06K 9/00* (2006.01)
*G01T 1/164* (2006.01)

(52) U.S. Cl.
CPC .................................. *G01T 1/1644* (2013.01)

USPC ............ 600/431; 600/425; 600/436; 378/21; 382/131

(58) Field of Classification Search
USPC ................. 600/407, 431, 436, 425; 424/1.11; 378/37, 21; 382/128, 131
See application file for complete search history.

(56) References Cited

U.S. PATENT DOCUMENTS 5,252,830 A     10/1993 Weinberg
5,261,406 A *   11/1993 MacKay et al. .............. 600/431
(Continued)

OTHER PUBLICATIONS

Schulte et al., "Grading of Tumors and Tumorlike Lesions of Bone: Evaluation by FDG PET", J Nucl Med., vol. 41, No. 10, Oct. 1, 2000, pp. 1695-1701.*

(Continued)

*Primary Examiner* — Katherine Fernandez
(74) *Attorney, Agent, or Firm* — Yakov Sidorin; Quarles & Brady LLP (57) ABSTRACT

A system and method for performing quantitative lesion analysis in molecular breast imaging (MBI) using the opposing images of a slightly compressed breast that are obtained from the dual-head gamma camera. The method uses the shape of the pixel intensity profiles through each tumor to determine tumor diameter. Also, the method uses a thickness of the compressed breast and the attenuation of gamma rays in soft tissue to determine the depth of the tumor from the collimator face of the detector head. Further still, the method uses the measured tumor diameter and measurements of counts in the tumor and background breast region to determine relative radiotracer uptake or tumor-to-background ratio (T/B ratio).

17 Claims, 5 Drawing Sheets

(56) References Cited

U.S. PATENT DOCUMENTS

| | | | |
|---|---|---|---|
| 5,323,006 A | 6/1994 | Thompson et al. | |
| 5,519,221 A | 5/1996 | Weinberg | |
| 5,965,891 A | 10/1999 | Weinberg | |
| 6,377,838 B1 | 4/2002 | Iwanczyk et al. | |
| 6,545,280 B2 | 4/2003 | Weinberg | |
| 6,740,882 B2 | 5/2004 | Weinberg | |
| 6,751,290 B2 * | 6/2004 | Salb | 378/98.9 |
| 6,771,802 B1 * | 8/2004 | Patt et al. | 382/128 |
| 7,102,134 B2 | 9/2006 | Weinberg | |
| 7,711,409 B2 * | 5/2010 | Keppel et al. | 600/436 |
| 2003/0108147 A1 * | 6/2003 | Kojima et al. | 378/19 |
| 2004/0015075 A1 * | 1/2004 | Kimchy et al. | 600/424 |
| 2005/0232474 A1 * | 10/2005 | Wei et al. | 382/128 |

OTHER PUBLICATIONS

International Search Report and Written Opinion under date of mailing of Jul. 3, 2008 corresponding to PCT/US2007/096991.

Molecular Breast Imaging Using a Dedicated High-Performance Instrument (O'Connor et al), Proc. of SPIE vol. 6319 6319D (Aug. 2006), p. 8, para 4; para 10, para 2; Table 3: Fig. 2, 10 and 12.

A Compact, discrete CsI(Tl) scintilator/Si photodiode gamma camera for breast cancer imaging: (Gruber). dissertation [online[. (Dec. 1, 2000). Lawrence Berkeley National Laboratory. Paper LBNL-47620. [retrieved on Jun. 22, 2008]. Retrieved from the Internet URL: http://repositories.cdlib.org/lbnl/LBNL-47620. p. 11, para 2; p. 118, para 2 and p. 119, para 1.

\* cited by examiner

SYSTEM AND METHOD FOR QUANTITATIVE MOLECULAR BREAST IMAGING

CROSS-REFERENCE TO RELATED APPLICATIONS

The present application is based on U.S. Provisional Patent Application Ser. No. 60/869,419, entitled "Quantitative Molecular Breast Imaging Using Dual Head Gamma Cameras," filed Dec. 11, 2006, and claims the benefit thereof.

STATEMENT REGARDING FEDERALLY SPONSORED RESEARCH

This invention was made with government support under Grant No. CA110162 awarded by the National Cancer Institute. The United States Government has certain rights in this invention.

FIELD OF THE INVENTION

The invention relates to a system and method for obtaining quantitative information regarding breast images acquired using gamma cameras.

BACKGROUND OF THE INVENTION

Screening mammography has been the gold standard for breast cancer detection for over 30 years, and is the only available screening method proven to reduce breast cancer mortality. However, the sensitivity of screening mammography varies considerably. The most important factor in the failure of mammography to detect breast cancer is radiographic breast density. In studies examining the sensitivity of mammography as a function of breast density, it has been determined that the sensitivity of mammography falls from 87-97 percent in women with fatty breasts to 48-63 percent in women with extremely dense breasts.

Diagnostic alternatives to mammography include ultrasound and MRI. The effectiveness of whole-breast ultrasound as a screening technique does not appear to be significantly different from mammography. MRI has a high sensitivity for the detection for breast cancer and is not affected by breast density. However, since bilateral breast MRI is currently approximately 20 times more expensive than mammography, it is not in widespread use as a screening technique.

Another prior-art technology is positron emission mammography (PEM). This uses two, small, opposing PET detectors to image the breast. The PEM technology offers excellent resolution; however, the currently available radiotracer (F-18 Fluoro deoxyglucose) requires that a patient fast overnight, the patient must have low blood levels (this is often a problem for diabetics), and after injection, the patient must wait 1-2 hours for optimum uptake of F-18FDG in the tumor. The high cost of these PET procedures coupled with the long patient preparation time reduces the usefulness of this procedure and makes it difficult to employ for routine breast evaluation.

Radionuclide imaging of the breast (scintimammography) with Tc-99m sestamibi was developed in the 1990s and has been the subject of considerable investigation over the last 10-15 years. This functional method is not dependent upon breast density. Large multi-center studies have shown the sensitivity and specificity of scintimammography in the detection of malignant breast tumors to be approximately 85 percent. However, these results only hold for large tumors and several studies have shown that the sensitivity falls significantly with tumor size. The reported sensitivity for lesions less than 10-15 mm in size was approximately 50 percent. This limitation is particularly important in light of the finding that up to a third of breast cancers detected by screening mammography are smaller than 10 mm. Prognosis depends on early detection of the primary tumor. Spread of a cancer beyond the primary site occurs in approximately 20-30 percent of tumors 15 mm or less in size. However, as tumor size grows beyond 15 mm, there is an increasing incidence of node positive disease, with approximately 40 percent of patients having positive nodes for breast tumors 2 cm in diameter. Hence, for a nuclear medicine technique to be of value in the primary diagnosis of breast cancer, it must be able to reliably detect tumors that are less than 15 mm in diameter. The failure of conventional scintimammography to meet this limit led to its abandonment as a useful technique in the United States.

In an attempt to overcome the limitation of conventional scintimammography, several small field-of-view gamma cameras have been developed that permit the breast to be imaging in a similar manner and orientation to conventional mammography. One commercial system for single photon imaging that is currently available is that manufactured by Dilon Technologies of Newport News, Va. Using a small detector and compression paddle, they reported a sensitivity of 67 percent for the detection of sub-10 mm lesions.

These systems employ a small gamma-ray camera that is attached to a mammography unit or to a stand-alone system in such a way that the gamma-ray camera is proximate to or in direct contact with a breast compression system. The system includes two identical opposing CZT detectors and performs planar imaging of the breast under compression. Recent clinical studies with the dual-head system have shown an increase in sensitivity to nearly 90 percent for lesions less than 10 mm.

Despite this improved percentage of success, the failure to identify lesions of any size can have significant consequences. Accordingly, it would be desirable to have a system and method to provide additional information to aid in the process of diagnosis, analysis, and treatment planning.

SUMMARY OF THE INVENTION

The present invention provides a system and method for performing quantitative tumor analysis using information acquired with a dual-headed molecular breast imaging system. Specifically, the present invention provides systems and method to utilize the information available in planar dedicated breast imaging to provide previously unavailable information sets to aid in the diagnosis and biopsy of the site. In particular, the present invention provides a method for accurately determining the size, depth to the collimator, and relative tracer uptake of a tumor.

In order to measure the diameter of a tumor, the present invention uses the shape of the pixel intensity profiles through each tumor to determine tumor diameter. Also, the method uses knowledge of compressed breast thickness and the attenuation of gamma rays in soft tissue to determine the depth of the lesion from the collimator face of the detector. Further still, the present invention uses the measured lesion diameter and measurements of counts in the lesion and background breast region to determine relative radiotracer uptake or tumor-to-background ratio (T/B ratio).

Various other features of the present invention will be made apparent from the following detailed description and the drawings.

DETAILED DESCRIPTION OF THE INVENTION

Figure 1:
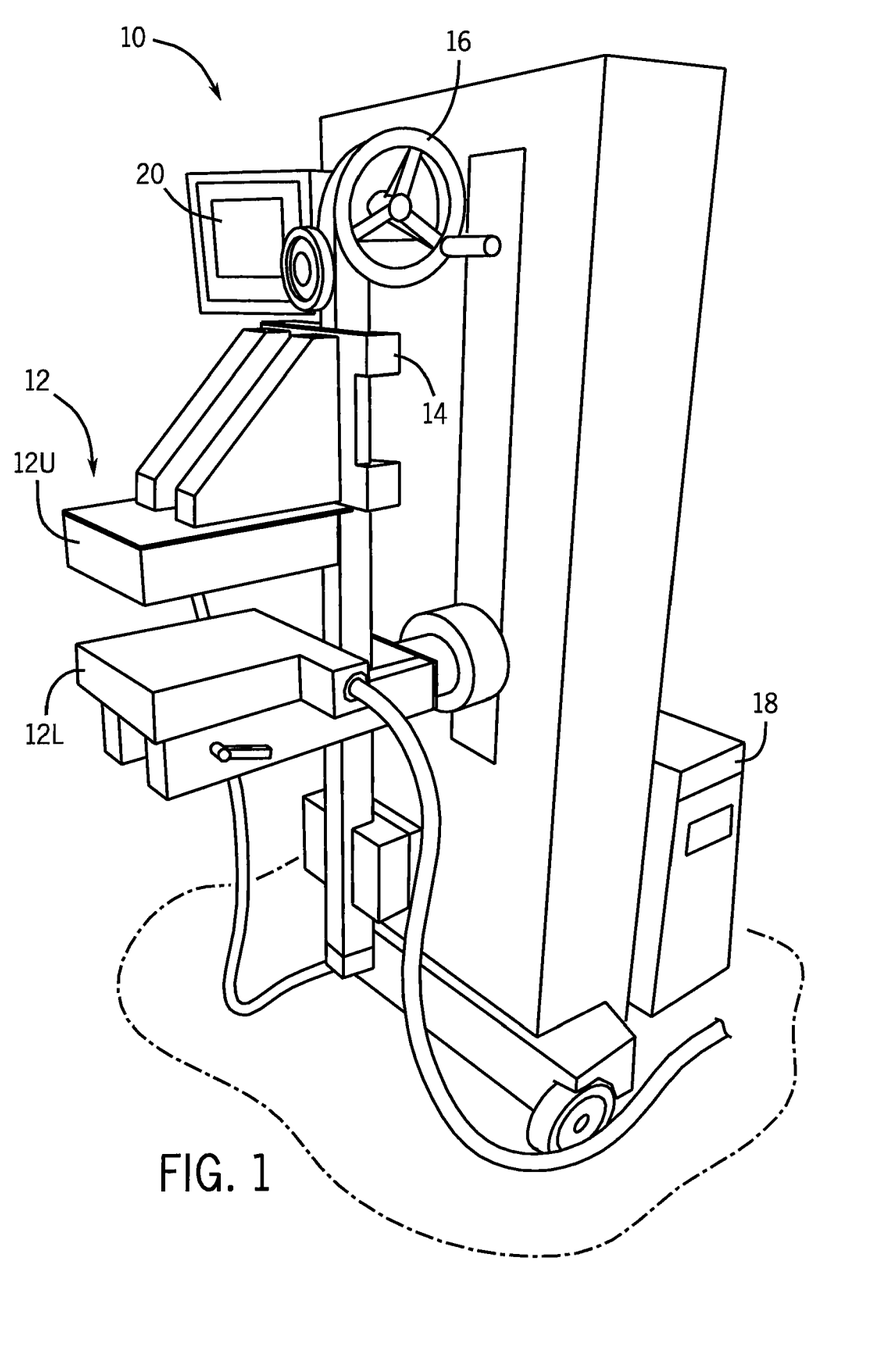
FIG. 1 is an illustration of a molecular breast imaging system for use with the present invention.

Referring to FIG. 1, a molecular breast imaging (MBI) system 10 includes two opposing cadmium zinc telluride (CZT) detectors (detector heads) 12. In particular, the detector heads 12 include an upper detector head 12U and a lower detector head 12L. Each detector head 12U, 12L is, for example, 20 cm by 16 cm in size and mounted on a modified upright type mammographic gantry 14. In accordance with one embodiment, the detector heads 12 are LumaGEM 3200S high-performance, solid-state cameras from Gamma Medica having a pixel size of 1.6 mm. LumaGEM is a trademark of Gamma Medica, Inc. Corporation of California.

The relative position of the detector heads 12 can be adjusted using a user control 16. Specifically, the detector head assemblies 12 are, preferably, designed to serve as a compression mechanism. Accordingly, this system configuration reduces the maximum distance between any lesion in the breast and either detector head 12 to one-half of the total breast thickness, potentially increasing detection of small lesions without additional imaging time or dose. The MBI system 10 includes a processor 18 for processing the signals acquired by the detector heads 12 to produce an image, which may be displayed on an associated display 20.

Figure 2:
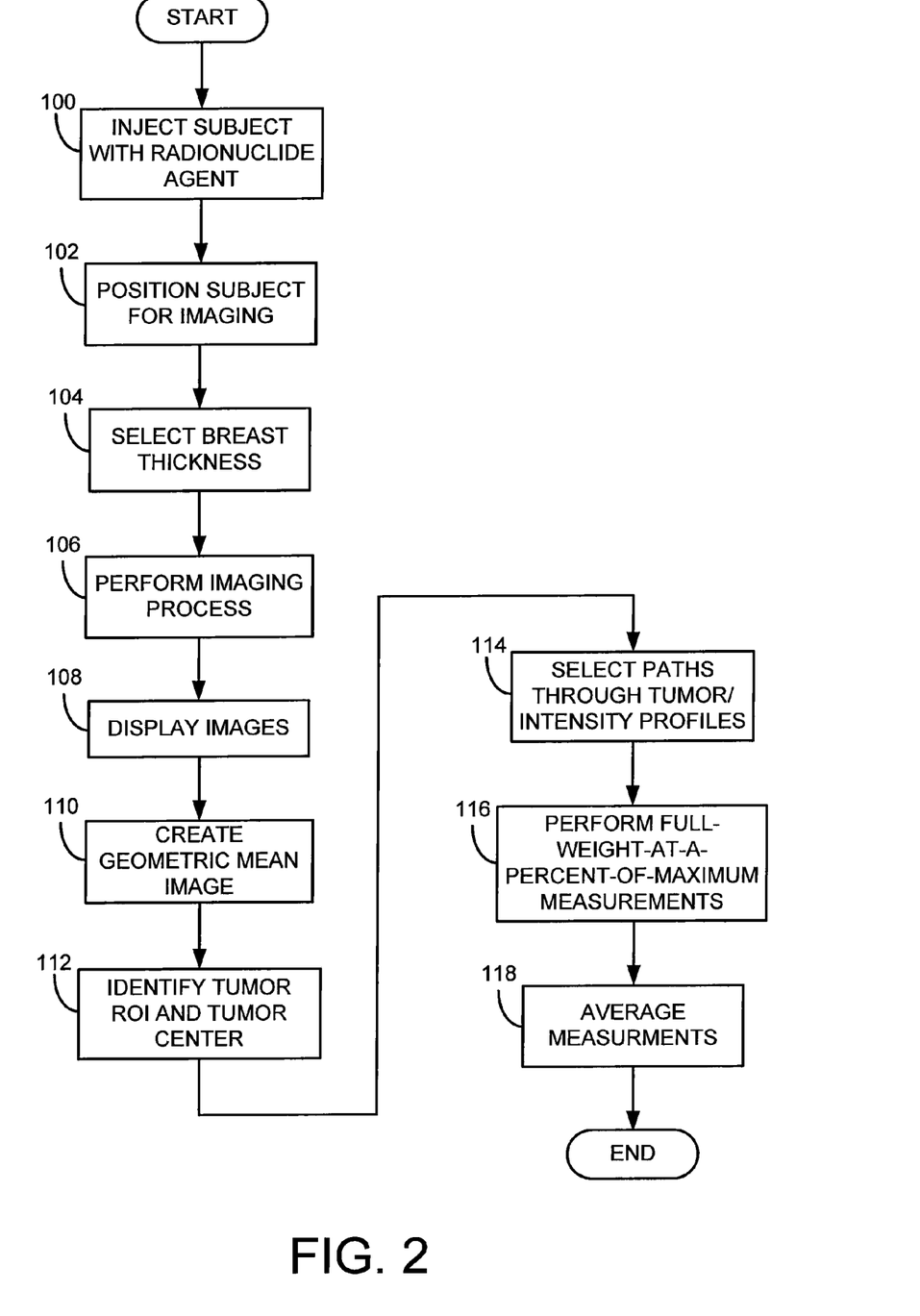
FIG. 2 is a flow chart setting forth the steps for determining a tumor size using the system of FIG. 1, in accordance with the present invention.

Referring to FIGS. 1 and 2, a process in accordance with the present invention begins at process block 100 by injecting a subject with a radionuclide imaging agent such as Tc-99m sestamibi (20 mCi/injection). The subject is then positioned for imaging at process block 102. Specifically, the subject is positioned so that a breast is arranged between the detector heads 12. The detector heads 12 are then adjusted using the user control 16 to lightly compress the breast between the upper detector head 12U and lower detector head 12L to improve image contrast and reduce motion artifacts. The compression amount is approximately ⅓ that of conventional mammography and is typically improves contrast and reduces motion artifacts.

Once the subject is properly positioned, the breast thickness is selected at process block 104. Specifically, the breast thickness may be automatically determined based on the relative position of the upper detector head 12U and the lower detector head 12L or an operator may enter the breast thickness through a user interface, the display 20.

At approximately 5 minutes post-injection, the breast is imaged at process block 106. An image is acquired by each detector head 12U, 12L of each breast at multiple views. For example, an image may be acquired in craniocaudal (CC) and mediolateral oblique (MLO) positions for 10 minutes per view. Furthermore, it is contemplated that imaging may be performed at multiple directions using both the craniocaudal and mediolateral oblique breast views to obtain a three-dimensional estimate of tumor size.

At each view, the images are simultaneously acquired by the upper detector head 12U and the lower detector head 12L. Thus, for each breast, multiple sets of data are acquired that are processed by the processor 18 and then shown to the operator on the display 20 or other viewing locality at process block 108. At a minimum, it is contemplated that the operator visually evaluates the four images (lower CC, upper CC, lower MLO, upper MLO) acquired of each breast.

In addition to the images described above, it is contemplated that at least one additional image may be generated at process block 110 that is a geometric mean image of the two opposing images. As a lesion moves deeper in the breast or farther away from a given detector head 12U or 12L, the diameter of the lesion increases due to the isotropic nature of the emitted photons. For example, a lesion closer to the lower detector head 12L appears smaller in the image acquired by the lower detector head 12L than in the image acquired by the upper detector head 12U. The geometric mean image of the two opposing images created at process block 110 provides a consistent lesion size on which to perform a measurement of the size of an identified tumor for a given breast thickness. Therefore, within the geometric mean image, a given tumor has a contrast indicative of the tumor being positioned in the middle of the breast, at half the total compressed breast thickness.

Using these images, any tumors appearing in the images are identified at process block 112 by selecting a tumor region of interest (ROI) including the tumor and indicating the center 206 of the tumor 204. For example, referring to FIG. 3, an image 200 may be displayed for an operator to select a tumor ROI 202 including evidence of a tumor 204 in the displayed image 200. Also, it is contemplated that the system may attempt to automatically identify the tumor(s) 204 within a given image or images 200 and select a preliminary ROI 202.

Figure 3:
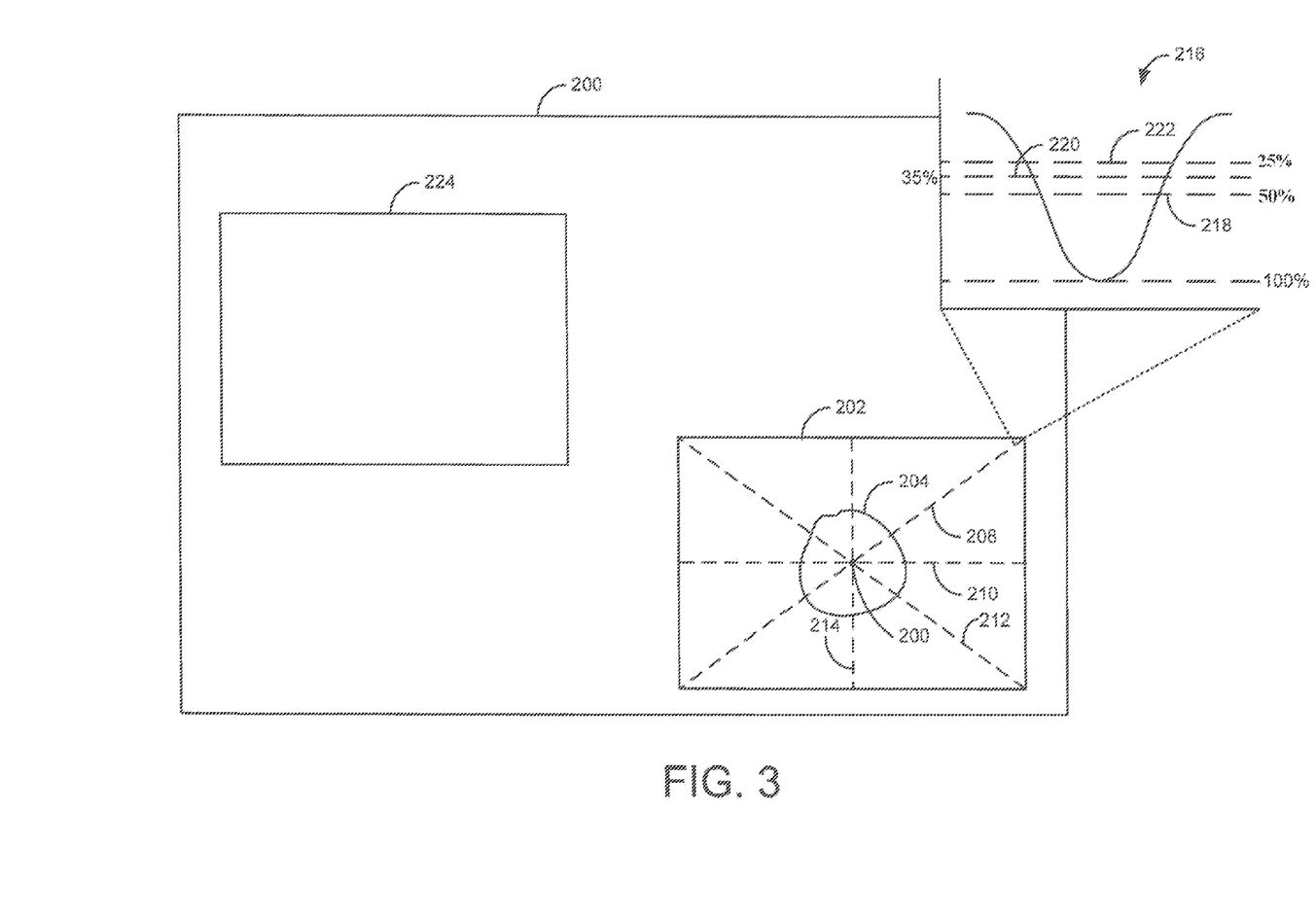
FIG. 3 is a schematic representation of a user interface for determining tumor size in accordance with the present invention.

Referring now to FIGS. 2 and 3, with this information entered, a plurality of paths 208-214 that extend through the tumor locations/centers 204/206 are selected at process block 114. In accordance with one embodiment, at least four paths at 0, 45, 90, and −45 degrees are obtained. However, the accuracy of the size measurement can be improved by using a larger number of paths through the tumor 202 and corresponding intensity profiles. That is, as illustrated in FIG. 3, these paths 208-214 have corresponding intensity profiles 216. For each intensity profile 216, a number of full-width-at-a-percentage-of-maximum measurements 218-22 are performed at process block 116. In particular, full widths of each profile at a variety of percentages of the maximum value are measured at process block 116. For example, the full width of each profile at 10, 15, 20, 25, 30, 35, 40, and 50 percent of the maximum value can measured. However, such a large sample is not typically necessary and the full widths at, for example, 25, 35, and 50 percent may be used. Regardless of the specific number of measurements obtained, the measurements are averaged at process block 118 to provide an average measurement metric indicating the diameter/size of the identified tumor 204.

Figure 4:
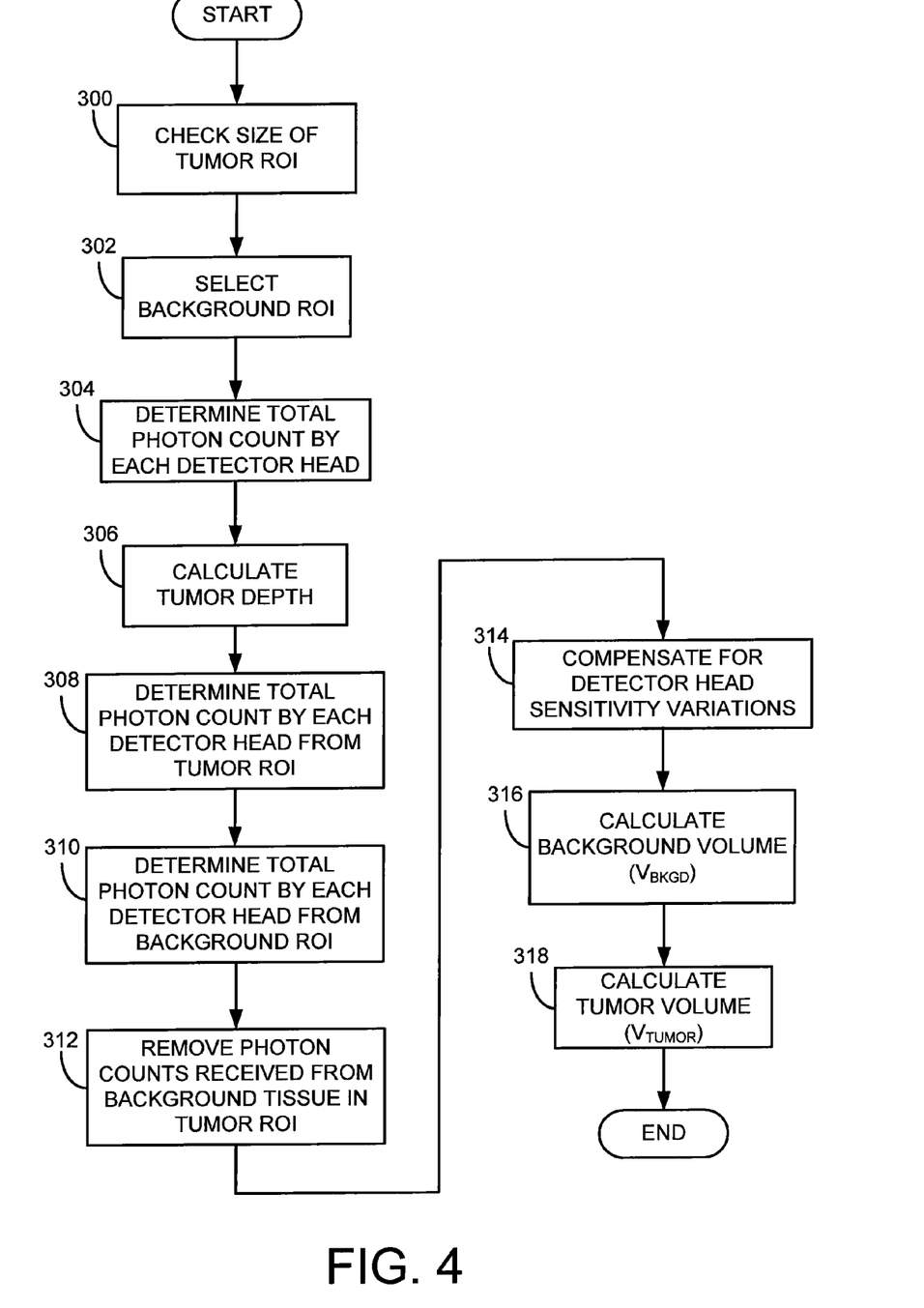
FIG. 4 is a flow chart setting for the steps for determining tumor depth and relative radiotracer uptake in accordance with the present invention.

Continuing with respect to FIGS. 1 and 4, the present method described with respect to FIG. 2 can be expanded to determine the depth of an identified tumor with respect to the lower (or upper) collimator face. The method begins at process block 300 by checking the size of the tumor ROI 202 selected at process block 112 of FIG. 2. Specifically, the ROI size applied to each tumor must be large enough to include nearly all of the photon counts received from the tumor 204 by both the upper and lower detector heads and to yield the corresponding images.

Figure 5:
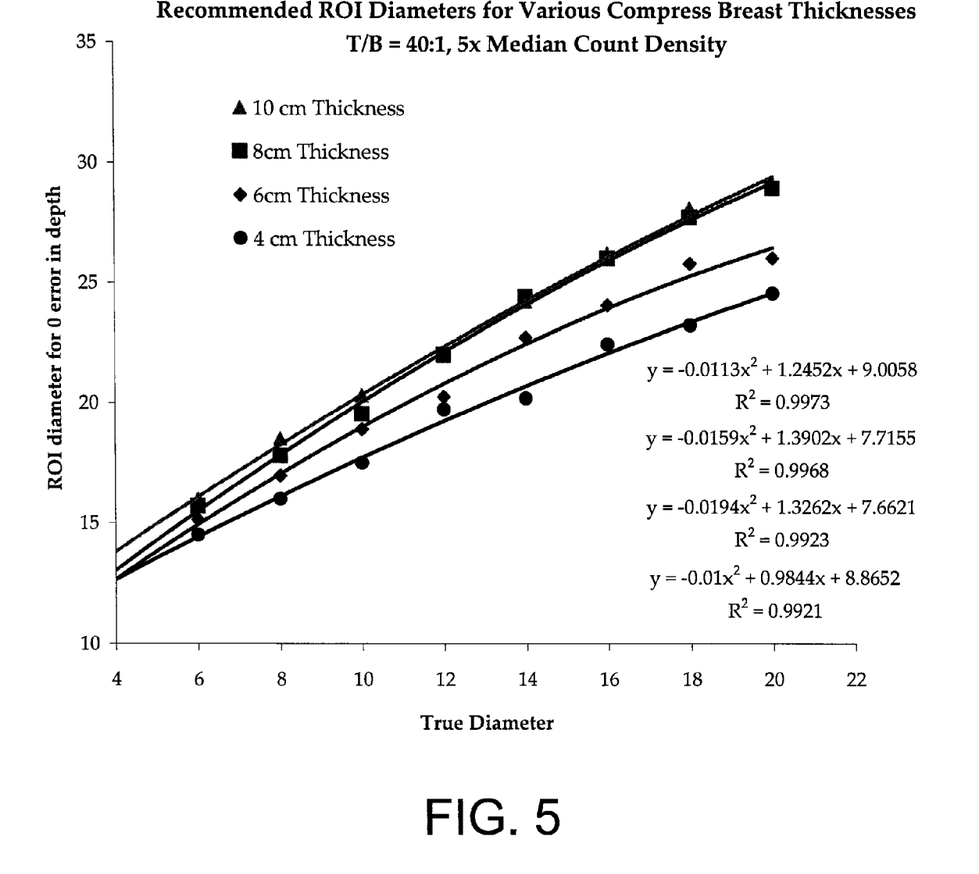
FIG. 5 is a plot showing diameters of regions of interest versus thickness value of breast compressed in an embodiment of the molecular breast imaging system.

To test the appropriate ROI size, the error in measured tumor depth was plotted as a function of ROI diameter. For each tumor diameter, there is a range of appropriate ROI diameters that produce a low (±1 mm) error in tumor depth. The zero crossing of each curve was used to determine the best ROI diameter to use for tumor depth measurement. FIG. 5 shows the ROI diameters that produced the minimum error in measured depth for tumor diameters of 4-20 mm and breast thicknesses of 4, 6, 8, and 10 cm.

To facilitate more precise placement of tumor ROIs, images can be interpolated by factors of 10 using a linear interpolation algorithm to resample the images with an adjusted pixel size, for example, 0.16×0.16 mm². The linear algorithm calculates the resampled pixel intensities by examining the neighboring intensities of the original image and integrating them based on their proportional distance from the projected resampling position.

Referring again to FIGS. 3 and 4, once an appropriate size of the tumor ROI 202 has been confirmed, a background ROI 224 is selected at process block 302. Specifically, the reference or background ROI 224 is selected to have the same size dimensions of the tumor ROI 202, but include only background tissue that is substantially free of tumor(s).

Once the tumor and background ROIs 202, 224 have been selected, at process block 304, the number of photons received at each detector head during the imaging process is determined. The photon counts made by the lower detector head 12L and upper detector head 12U are represented as $N_L$ and $N_U$, respectively, as follows:

$$N_L = N_O \cdot \exp(-\mu d) \qquad \text{Eqn. 1};$$

$$N_U = N_O \cdot \exp(-\mu(t-d)) \qquad \text{Eqn. 2};$$

where $N_O$ is the number of unattenuated photons determined at process block 304, $\mu$ is a known attenuation coefficient of soft tissue (0.153 cm$^{-1}$), t is compressed breast thickness determined at process block 104 of FIG. 2, and d is tumor depth to be determined. Using these photon counts, a tumor depth calculation is performed at process block 306 by solving for d in Eqns. 1 and 2. Specifically, Eqns. 1 and 2 are solved for $N_o$ and then set equal to each other to yield the following equation for tumor depth, d:

$$d = \frac{\mu t - \ln\left(\frac{N_L}{N_U}\right)}{2\mu}. \qquad \text{Eqn 3}$$

Thereafter, a further refined depth measurement can be provided by removing photon counts provided by background structures in the ROI. Specifically, the sum of photon counts received from the tumor ROI identified at process block 212 of FIG. 2 and confirmed at process block 300 of FIG. 4 is calculated for each detector head at process block 308. Thereafter, at process block 310, the sum of photon counts received from the background ROI is calculated for each detector head at process block 310. With this additional information, Eqn. 3 can be modified to account for photon counts only coming from the tumor. Specifically, at process block 312, the total background photon counts received from the background ROI is subtracted from the total photon counts received from the tumor ROI to remove the photon counts from the tumor ROI that are attributable to background tissue. Also, at process block 314, a correction can be applied to the photon counts from upper detector head 12U (or, alternatively, to the lower detector head 12L if the upper detector head 12U is used as the reference frame from which the depth measurement is made) to adjust for possible differences in detector sensitivity. The steps taken at process bocks 312 and 314 are achieved by modifying Eqn. 3 yield the following:

$$d = \frac{\mu t - \ln\left(\frac{T_L - B_L}{(T_U - B_U) \cdot \frac{B_L}{B_U}}\right)}{2\mu}; \qquad \text{Eqn. 4}$$

where $T_L$ and $T_U$ are the sum of photon counts received from an identical ROI placed on the tumor in the images provided by the lower detector head 12L and upper detector head 12U, respectively, and $B_L$ and $B_U$ are the sum of photon counts received from an ROI of equal size placed in a uniform background breast tissue region of the image provided by the lower detector head 12L and upper detector head 12U, respectively.

Additionally, using the ROI size determined as described above, photon counts in the tumor and background ROIs can be used to calculate a tumor to background (T/B) uptake ratio. To do so, the process continues by calculating a background volume ($V_{bkgd}$) at process block 316. Specifically the area of the background ROI selected at process block 302 is multiplied by the thickness of the breast determined at process block 104 of FIG. 2 to yield the background volume. Then, a tumor volume ($V_{tumor}$) is calculated at process block 318 using the tumor size/diameter calculated as described above with respect to FIG. 2. The T/B ration is therefore calculated as follows:

$$T/B \text{ Ratio} = \frac{\sqrt{(T_L \cdot T_U)} - \sqrt{(B_L \cdot B_U)}}{\sqrt{(B_L \cdot B_U)}} \cdot \frac{V_{Bkgd}}{(V_{Tumor})^F}; \qquad \text{Eqn. 5}$$

where F is a constant of 0.99 that was empirically determined to provide a more accurate measure of T/B ratio. In accordance with one embodiment of the invention, it is contemplated that the tumor volume may be estimated by assuming a spherical tumor shape using the tumor diameter determined as described above with respect to FIG. 2. However, as described above, to more accurately determine the volume of non-spherical lesions, a higher number of intensity profiles extending in multiple directions through the tumor, using both the craniocaudal and mediolateral oblique breast views, could be used to obtain a better estimate of tumor size. In any case, Eqn. 5 is the ratio of the geometric mean of the tumor regions to the geometric mean of the background regions with corrections for differences in the ROI volumes.

It is noted that one advantage of the present invention is that the specific pixel size used results in statistically insignificant changes in the measured diameter, depth, and T/B ratio. However, both the depth and the T/B ratio measurements are dependent on an accurate measurement of tumor size/diameter. While Eqn. 4 does not directly depend on the size/diameter measurement, the ROI size used to perform the depth measurement is determined from the previously measured tumor size. Also, as described above with respect to Eqn. 5, the T/B ratio is directly dependent on tumor volume, which is calculated using the measured tumor size/diameter.

To quantify the dependence of depth and T/B ratio calculations on the size/diameter measurement, calculations for depth and T/B ratio were performed on a set of Monte-Carlo simulated, dual-head images after setting the tumor diameter to 1 mm greater and 1 mm less than the known true diameter for each tumor. These images were acquired with a 6 cm breast thickness, a tumor depth of 2 cm from the lower detector, and a T/B of 40:1. The expected change in T/B measurement was calculated by manipulating Eqn. 5 as follows:

$$T/B \text{ Ratio} \propto \frac{1}{(V_{Tumor})^F} = \frac{1}{\left[\frac{4}{3}\pi\left(\frac{d}{2}\right)^3\right]^{.99}}; \quad \text{Eqn. 6}$$

which shows that T/B ratio is inversely proportional to the tumor volume raised to the factor F=0.99. Therefore, T/B ratio is inversely proportional to diameter, d, cubed and raised to the power of 0.99 as shown in Eqn. 6. The change in T/B ratio for a given fraction of the true diameter can thus be calculated as follows:

$$\text{Change in } T/B \text{ Ratio} = \frac{1}{(k^3)^{.99}}; \quad \text{Eqn. 7}$$

where k is the fraction of the true diameter. For example, if tumor diameter is underestimated by 5%, k=0.95 and the change in T/B is 1.165, or T/B is overestimated by 16.5%. Nevertheless, the percent error in the calculated T/B ratio was tested to show the absolute average error in T/B ratio can be controlled to be less than 5% for all breast thicknesses, except at the T/B of 10:1, where error was nearly 9% at a 4 cm breast thickness.

Therefore, while depth measurements are nearly unchanged for small errors in the diameter measurement, T/B ratio can be significantly affected by a large percent error in the diameter measurement. However, as noted above, the accuracy of the diameter measurement can be improved by using more than a larger number of intensity profiles through the tumor.

Therefore, the present invention provides a method for performing quantitative tumor analysis using information acquired with a dual-headed molecular breast imaging system. Specifically, the present invention provides a method for accurately determining the size, depth to the collimator, and relative tracer uptake of a tumor. While determination of these parameters was previously only possible with tomographic imaging methods, the present invention is able to utilize the information available in planar dedicated breast imaging to provide these previously unavailable information sets to aid in the diagnosis and biopsy of the site.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for analyzing molecular breast images comprising the steps of:
   a) injecting a radionuclide imaging agent into a subject to be imaged;
   b) compressing a breast of the subject between two opposing, planar gamma detectors, said breast containing a tumor;
   c) acquiring a number of photons from so compressed breast at each of said gamma detectors to create at least one two-dimensional image representing said compressed breast;
   d) identifying a two-dimensional tumor image region in said at least one two-dimensional image;
   e) determining a plurality of intensity profiles, each intensity profile from said plurality of intensity profiles being determined along a respectively corresponding path extending across said two-dimensional tumor image region; and
   f) calculating, using a processor, a size of the tumor from said plurality of intensity profiles
   wherein said calculating includes:
      calculating a plurality of size metrics from each intensity profile of said plurality of intensity profiles, wherein different size metrics from said plurality of size metrics are calculated at different percentage-of-maximum levels of a corresponding intensity profile; and
      averaging said plurality of size metrics to generate an average size metric indicating said size of the tumor along a path associated with said corresponding intensity profile.

2. The method of claim 1 further comprising
   g) determining a number of unattenuated photons received by each of said gamma detectors from the ROI; and
   h) determining a depth of the tumor in the breast using the number of photons acquired in step c), the number of unattenuated photons determined in step g), and an attenuation coefficient of tissue in the breast.

3. The method of claim 2 wherein step d) includes
   d)i) identifying corresponding tumor ROIs including the tumor and
   d)ii) identifying corresponding background ROIs not including the tumor.

4. The method of claim 3 further comprising i) calculating a tumor-to-background ratio based on a sum of photon counts received from tumor ROIs identified in step d)i) and a sum of photon counts received from background ROIs identified in step d)ii).

5. A method for a computerized analysis of molecular breast images comprising the steps of:
   a) injecting a radionuclide imaging agent into a subject to be imaged;
   b) positioning a breast of the subject between two opposing, planar gamma detectors;
   c) determining a thickness of the breast between the gamma detectors;
   d) acquiring, along a single spatial direction, numbers of photons emitted from the breast with each of the gamma detectors to create respective images of the breast;
   e) identifying a tumor and a surrounding ROI in at least one of the respective images of the breast;
   f) calculating numbers of unattenuated photons received, along said single spatial direction, by each of the gamma detectors from the ROI; and
   g) determining a depth of the tumor in the breast using the numbers of photons acquired in step d), the numbers of unattenuated photons determined in step f), and an attenuation coefficient of tissue in the breast.

6. The method of claim 5 wherein step g) includes determining the depth of the tumor according to:

$$d = \frac{\mu t - \ln\left(\frac{N_L}{N_U}\right)}{2\mu};$$

where $N_L$ and $N_U$ represent numbers of photons acquired with respective gamma detectors in step d), $\mu$ represents the attenuation coefficient of tissue in the breast, t represents a compressed breast thickness after step b), and d represents the depth of the tumor from at least one of the gamma detectors.

7. The method of claim 5 wherein step e) includes displaying an interpolated image created using a linear interpolation algorithm to resample said at least one of the respective images of the breast at an adjusted pixel size.

8. The method of claim 5 wherein
step e) includes
 e)i) identifying corresponding first ROIs in each of the respective images of the breast including the tumor and
 e)ii) identifying corresponding second ROIs in each of the respective images of the breast, the second ROIs including only background tissue that is substantially free of the tumor; and
step g) includes determining the depth of the tumor according to:

$$d = \frac{\mu t - \ln\left(\frac{T_L - B_L}{(T_U - B_U) \cdot \frac{B_L}{B_U}}\right)}{2\mu};$$

wherein
 $\mu$ represents the attenuation coefficient of tissue in the breast, t represents a thickness of the breast compressed after step b);
 $T_L$ and $T_U$ respectively represent sums of photons received from the corresponding first ROIs identified in step e)i) by first and second planar detectors of said gamma detectors;
 $B_L$ and $B_U$ respectively represent sums of photons received from the corresponding second ROIs identified in step e)ii) by first and second planar detectors of said gamma detectors; and
 d represents the depth of the tumor from at least one of said gamma detectors.

9. The method of claim 8 wherein the first ROIs identified, in a respective image of the breast, in step e)i) and the second ROIs identified, in said respective image of the breast, in step e)ii) have substantially similar size.

10. The method of claim 8 wherein
step f) includes selecting a plurality of intensity profiles, each intensity profile determined along a respectively corresponding path extending, in at least one of said respective images, across the tumor; and
step g) includes calculating a size of the tumor based on the plurality of intensity profiles selected in step f).

11. The method of claim 10 further comprising h) calculating a ratio of a geometric mean of tumor regions in the first ROIs identified in step e)i) to a geometric mean of background regions in the second ROIs identified in step e)ii).

12. The method of claim 11 wherein step h) includes calculating a tumor to background (T/B) uptake ratio according to:

$$T/B \text{ Ratio} = \frac{\sqrt{(T_L \cdot T_U)} - \sqrt{(B_L \cdot B_U)}}{\sqrt{(B_L \cdot B_U)}} \cdot \frac{V_{Bkgd}}{(V_{Tumor})^F};$$

where $V_{Bkgd}$ represents an area of tissue included in the ROIs identified in step e)ii) multiplied by the breast thickness t, $V_{Tumor}$ is an estimated tumor volume calculated using the size calculated in step g), and F is an empirically-determined constant.

13. The method of claim 5, wherein said acquiring numbers of
photons emitted from the breast to create respective images of the breast includes
 acquiring numbers of photons emitted from the breast with each of said gamma detectors to create respective two-dimensional images of the breast compressed between said planar gamma detectors; and
 determining intensity profiles extending across a tumor image region of at least one of said two-dimensional images.

14. The method of claim 13, further comprising
calculating a plurality of size metrics from each intensity profile, wherein different size metrics are calculated at different percentage-of-maximum levels of a corresponding intensity profile.

15. A method for analyzing molecular breast images comprising the steps of:
 a) injecting a radionuclide imaging agent into a subject to be imaged;
 b) positioning a breast of the subject between two opposing, planar gamma detectors, the breast including a tumor;
 c) acquiring a number of photons from said breast at each of the gamma detectors to create at least one two-dimensional image representing said breast;
 d) identifying a tumor region in said at least one two-dimensional image;
 e) selecting, in said at least one two-dimensional image, a first ROI including the tumor region;
 f) selecting, in said at least one two-dimensional image, a second ROI equal in size to the first ROI but including only background tissue that is substantially free of tumors;
 g) determining a plurality of intensity profiles, each intensity profile determined along a corresponding path extending across the tumor region in said at least one two-dimensional image;
 h) calculating, using a processor, a size of said tumor region in said at least one two-dimensional image based on said plurality of intensity profiles,
  wherein said calculating a size of said tumor region includes calculating a plurality of size metrics from each intensity profile of said plurality of intensity profiles,
  wherein different size metrics from said plurality of size metrics are calculated at different percentage-of-maximum levels of a corresponding intensity profile;
 i) determining a volume of the tumor based on said size of the tumor region; and
 j) calculating a tumor-to-background ratio based on tumor regions present in the first ROI and background regions present in the second ROI.

16. The method of claim 15 further comprising
 k) determining a number of unattenuated photons received by each of the gamma detectors from the first ROI; and
 l) determining a depth of the tumor in the breast using the number of photons acquired in step c), the number of unattenuated photons determined in step k), and an attenuation coefficient of tissue in the breast.

17. The method of claim 15, wherein step h) further includes averaging said plurality of size metrics to generate an average size of the tumor along a path associated with the corresponding intensity profile.

* * * * *